(12) United States Patent
Bernhardt (10) Patent No.: US 11,510,649 B2
(45) Date of Patent: Nov. 29, 2022

(54) METHODS AND APPARATUSES FOR PROPHYLACTICALLY TREATING UNDETECTED KIDNEY STONES USING MECHANICAL WAVES PRODUCED FROM A TACTILE TRANSDUCER

(71) Applicant: Michael D. Bernhardt, Buffalo, NY (US)

(72) Inventor: Michael D. Bernhardt, Buffalo, NY (US)

( * ) Notice: Subject to any disclaimer, the term of this patent is extended or adjusted under 35 U.S.C. 154(b) by 407 days.

(21) Appl. No.: 15/960,999

(22) Filed: Apr. 24, 2018

(65) Prior Publication Data

US 2018/0303458 A1 Oct. 25, 2018

Related U.S. Application Data

(60) Provisional application No. 62/489,542, filed on Apr. 25, 2017.

(51) Int. Cl.
*A61B 8/00* (2006.01)
*A61B 5/00* (2006.01)
(Continued)

(52) U.S. Cl.
CPC .......... *A61B 8/4494* (2013.01); *A61B 5/6823* (2013.01); *A61B 5/6831* (2013.01);
(Continued)

(58) Field of Classification Search
CPC .............. A61B 8/4494; A61B 17/2251; A61B 17/22004; A61B 17/225; A61B 5/6831; A61B 5/6823; A61B 18/26; A61B 2018/00511; A61B 17/22–2256; A61H 23/008; A61H 23/0245; A61H 2201/5005; A61H 2201/5074; A61H 2201/1207; A61H 2201/1623; A61H 2201/5028; A61H 2203/0425; B06B 1/00–20; B06B 1/0284; G01B 9/02004; G01B 9/02031
See application file for complete search history.

(56) References Cited

U.S. PATENT DOCUMENTS

| 4,907,572 A | 3/1990 | Borodulin et al. |
| 7,418,108 B2 | 8/2008 | Oser |

(Continued)

FOREIGN PATENT DOCUMENTS

WO 2016/147125 A1 9/2016

*Primary Examiner* — Christopher Koharski
*Assistant Examiner* — Richmond J Van Winter
(74) *Attorney, Agent, or Firm* — Hamilton, Brook, Smith & Reynolds, P.C.

(57) ABSTRACT

Apparatuses and methods utilizing tactile transducers to create mechanical waves that travel through an individual's body to the kidneys to dislodge kidney stones. Embodiments include a structural member with at least one tactile transducer, an amplifier, and a controller. The tactile transducer(s) produce mechanical waves, and the structural member enables projection of the mechanical waves produced by the tactile transducer(s) toward at least one kidney to dislodge kidney stones. The amplifier is electronically coupled to the at least one tactile transducer, and the controller is electronically coupled to the amplifier and configured to determine the mechanical waves produced by the at least one tactile transducer.

19 Claims, 9 Drawing Sheets

(51) Int. Cl.
*A61B 18/00* (2006.01)
*A61B 17/22* (2006.01)
*A61B 17/225* (2006.01)
*A61H 23/00* (2006.01)
*A61H 23/02* (2006.01)
*A61B 18/26* (2006.01)

(52) U.S. Cl.
CPC ...... *A61B 17/22004* (2013.01); *A61B 17/225* (2013.01); *A61B 17/2251* (2013.01); *A61H 23/008* (2013.01); *A61H 23/0245* (2013.01); *A61B 18/26* (2013.01); *A61B 2018/00511* (2013.01); *A61H 2201/1207* (2013.01); *A61H 2201/1623* (2013.01); *A61H 2201/5005* (2013.01); *A61H 2201/5028* (2013.01); *A61H 2201/5074* (2013.01); *A61H 2203/0425* (2013.01)

(56) References Cited

U.S. PATENT DOCUMENTS

| | | | |
|---|---|---|---|
| 8,668,045 B2* | 3/2014 | Cohen | H04R 5/04 181/150 |
| 2010/0281944 A1* | 11/2010 | Brucke | G01L 25/00 73/1.15 |
| 2011/0034832 A1* | 2/2011 | Cioanta | A61B 17/22004 601/1 |
| 2011/0263967 A1* | 10/2011 | Bailey | A61B 17/2256 600/453 |
| 2013/0253387 A1* | 9/2013 | Bonutti | A61B 17/24 601/46 |
| 2014/0336665 A1* | 11/2014 | Gavala | A61B 17/32002 606/128 |
| 2015/0063606 A1* | 3/2015 | Alexiou | H01L 41/193 381/151 |
| 2015/0296280 A1 | 10/2015 | Lee | |
| 2016/0120559 A1* | 5/2016 | Cao | A61B 17/2256 601/4 |
| 2019/0030568 A1* | 1/2019 | Broszeit | B08B 3/12 |

\* cited by examiner

METHODS AND APPARATUSES FOR PROPHYLACTICALLY TREATING UNDETECTED KIDNEY STONES USING MECHANICAL WAVES PRODUCED FROM A TACTILE TRANSDUCER

RELATED APPLICATION

This application claims the benefit of U.S. Provisional Application No. 62/489,542, filed on Apr. 25, 2017. The entire teachings of the above application are incorporated herein by reference.

BACKGROUND

Kidneys perform many functions, including filtering of blood and maintaining proper levels of certain minerals in blood. Kidney stones, a common affliction of the kidneys, can cause a person severe pain. There are several kinds of kidney stones, which vary by composition, but all are formed in essentially the same way. Kidney stones begin when the solute in supersaturated urine leaving the nephron precipitates out and forms a crystal in the tubule. If the crystal does not pass soon after and, instead, becomes stuck in the kidney, the crystal will act as a nidus (a place in which something is formed or deposited), and a kidney stone will grow. The pain of kidney stones is often caused when a crystal that has had the opportunity to grow detaches from where it grew, gets caught, and then blocks urine flow. Common sites of ureteric constriction are the pelviureteric junction, the pelvic brim, and the vesicoureteric junction. Between 1994 and 2007, the prevalence of kidney stones in the US increased from 1-in-20 persons to 1-in-11 persons, nearly doubling (see https://www.ncbi.nlm.nih.gov/pmc/articles/PMC3362665/). Because of the renal colic they cause, kidney stones are temporarily debilitating, frequently resulting in patients missing work. Soldiers, particularly when deployed to hot desert environments, are also prone to developing kidney stones, which can make the soldiers vulnerable in the field. Other than attempting to maintain a proper diet and proper hydration, there has been little one could do to prevent kidney stones from becoming stuck in the kidney and growing.

SUMMARY

The apparatuses and methods presented herein utilize mechanical waves to vibrate the kidneys to dislodge kidney stones. Dislodging the stones while they are relatively small allows the stones to pass through the kidney and ureters pain free. The apparatuses and methods can be used, for example, in a prophylactic manner when the stones first start forming so they pass painlessly while they are still small and perhaps unnoticed, or in concert with pain medications and alpha blockers in order to help larger stones that are causing a blockage to pass. The disclosed apparatuses and methods are noninvasive and require little to no medical training to operate.

According to an example embodiment, an apparatus for treating kidney stones includes a structural member with at least one tactile transducer, an amplifier, and a controller. The tactile transducer(s) produce mechanical waves, and the structural member enables projection of the mechanical waves produced by the tactile transducer(s) toward at least one kidney to dislodge kidney stones, e.g., the tactile transducer(s) can be mounted to the structural member such that mechanical waves produced by the tactile transducer(s) are projected toward (transferred to) the at least one kidney. The amplifier is electronically coupled to the at least one tactile transducer, and the controller is electronically coupled to the amplifier and configured to determine the mechanical waves to be produced by the at least one tactile transducer.

According to another example embodiment, an apparatus for administering mechanical waves to an individual includes a structural member with at least one tactile transducer, an amplifier, and a controller. The tactile transducer(s) produce mechanical waves, and the structural member enables projection of the mechanical waves produced by the tactile transducer(s) toward the individual. The amplifier is electronically coupled to the at least one tactile transducer, and the controller is electronically coupled to the amplifier and configured to determine the mechanical waves to be produced by the at least one tactile transducer.

The controller may cause the tactile transducer(s) to produce mechanical waves at a resonant frequency of kidney tissue, which may be in the range of, for example, nine to sixteen hertz. The controller can, in some configurations, cause the tactile transducer(s) to cycle through the frequency range of mechanical waves. In some embodiments, the structural member may be a band to be worn by an individual and to be arranged to position the tactile transducer(s) in a vicinity of at least one of the individual's kidneys. In other embodiments, the structural member may be a cushion (e.g., pillow) configured to allow an individual to position the individual's back against the cushion with the tactile transducer(s) in a vicinity of at least one of the individual's kidneys. In other embodiments, the structural member may be a chair, where the tactile transducer(s) are mounted to the chair so that the tactile transducer(s) are in a vicinity of an individual's kidneys when the individual is sitting in the chair. In other embodiments, the structural member may be a bench including a plurality of tactile transducers mounted to the bench, where each of the tactile transducers is arranged to be in the vicinity of at least one kidney of an individual sitting on the bench. In other embodiments, the structural member may be a bench, where the tactile transducer(s) are mounted to a bar spanning at least a portion of the length of the bench. When a plurality of individuals are sitting on the bench, the mechanical waves produced by the tactile transducer(s) propagate along the bar and toward at least one kidney of each of the individuals. In some embodiments, the structural member may include two tactile transducers mounted at locations corresponding to the positions of two kidneys. The tactile transducer(s) may be adjustably mounted to the structural member. In some embodiments, padding (e.g., acoustically appropriate padding) may be mounted to the at least one tactile transducer. In some embodiments, vibration isolator(s) may be mounted between the structural member and the tactile transducer(s).

According to another example embodiment, a method of treating kidney stones includes providing a structural member including at least one tactile transducer configured to produce mechanical waves, positioning an individual with respect to the structural member to enable the mechanical waves produced by the at least one tactile transducer to be projected toward (transferred to) at least one kidney of the individual to dislodge kidney stones from the at least one kidney, and causing the at least one tactile transducer to produce mechanical waves to dislodge kidney stones from the at least one kidney. The tactile transducer(s) can, in some embodiments, cycle through a range of frequencies, which can be, for example, a range of nine to sixteen hertz. The mechanical waves may be administered for a therapeutically effective duration, and the kidney(s) of the individual may be periodically subjected to the mechanical waves produced by the tactile transducer(s).

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows. The teachings of all patents, published applications, and references cited herein are incorporated by reference in their entirety.

The apparatuses and methods presented herein utilize tactile transducers to create mechanical waves (e.g., sound waves) that travel through an individual's body to the kidneys and/or associated ureters to loosen kidney stones. There are different types of transducers. For example, a speaker is a type of transducer that converts electrical energy (an audio signal) into mechanical energy (vibration of the speaker components). A tactile transducer also converts electrical energy into mechanical energy, but does not have to cause vibration of speaker components. A tactile transducer can be used to cause vibration of any object, including an individual or part of an individual (e.g., a kidney). While examples of apparatuses and methods presented herein utilize tactile transducers, the apparatuses and methods can, alternatively, or additionally, use audio speakers.

Kidneys are retroperitoneal organs, located outside of the peritoneum, found along the posterior muscular wall of the abdominal cavity, one on each side of the spine. They are surrounded by perirenal fat, which protects them with help from the muscles and ribs of the back. Mechanical waves (e.g., sound waves) transport energy through a medium, without transporting the medium itself. The waves, traveling through this muscle and fat medium, work to dislodge the stones by causing the kidneys to vibrate. As the frequency of the waves approaches the resonant frequency of kidneys, the waves cause the kidneys to vibrate. One study/journal article has found that the resonant frequencies of standing humans ranges from 9 to 16 Hz (see https://www.ncbi.nlm.nih.gov/pubmed/9306739). A device that is capable of producing such a range of frequencies can be used effectively for all individuals by accounting for variations from individual to individual. Some embodiments may cycle through the range of such resonant frequencies. For example, one embodiment may use a frequency of 9 Hz for five seconds, 10 Hz for five seconds, 11 Hz for five seconds, and so on through 16 Hz, and repeat the cycle for the duration of the treatment. The amount of the step (1 Hz, 0.5 Hz, etc.) and the duration of each step can be different from embodiment to embodiment. As a further example, another embodiment may continuously change the frequency used throughout the treatment, ramping from 9 Hz to 16 Hz. The cycle may be repeated any arbitrary number of times throughout the treatment.

When there is a blockage due to a developed kidney stone, use of sound waves with alpha blockers that relax the smooth muscle of ureters can cause a relatively spontaneous result due to a combination of vibrations distorting the relaxed ureters and the pressure created by the backup of urine. The apparatuses and methods presented herein may be employed for a relatively short amount of time (in the range of minutes). As an example comparison, roller coasters have been found to help dislodge kidney stones, and roller coaster rides generally last only a couple of minutes or less (see https://www.theatlantic.com/health/archive/2016/09/for-kidney-health-roller-coaster-therapy/501278/). If one use does not have an immediate effect, three to four times per week can have a similar efficacy as intercourse at the same rate, which has been found to improve kidney stone expulsion by 60% in the first two weeks (see https://www.researchgate.net/publication/309894541_Evaluation_of_the_efficacy_of_sexual_intercourse_in_expulsion_of_distal_ureteric_stones).

Used prophylactically, once per month is likely sufficient for many individuals to continually expel small crystals that grow to form problem stones, as it has been found that in high risk environments, such as Kuwait and Iraq, the mean time to development of a symptomatic stone was 93 days in the hot desert environment (see http://www.jurology.com/article/S0022-5347(05)60358-8/abstract). People who have had a kidney stone in the past have a 50% chance of having another, so those individuals are excellent candidates for prophylactic use, and anyone transitioning into a high risk environment (e.g., a desert) would likely benefit as well.

The apparatuses presented herein can take many forms, many of which align tactile transducers with the kidneys, include an amplifier to power the tactile transducers, and a computer/circuitry to define/determine the waves created by the tactile transducers. Any padding covering the tactile transducers for comfort may be selected to be a good transmitter/propagator of mechanical waves (e.g., sound waves). Some embodiments include a bar coupled to the tactile transducer(s) to extend the tactile transducer's reach.

As illustrated and as described below, the apparatuses may take the form of a chair, as a pillow an individual can sit against, and as a belt/band that the individual can wear.

A larger setup to treat many people at once, with tactile transducers and/or tactile transducer(s) affixed to a bar, can take the form of a long bench or couch. In embodiments where the transducer(s) are mounted to a chair or other solid structure, it can be beneficial to isolate the transducer(s) from the structure. Apparatuses can receive power using a plug to insert into an electric source or using batteries.

Figure 1:
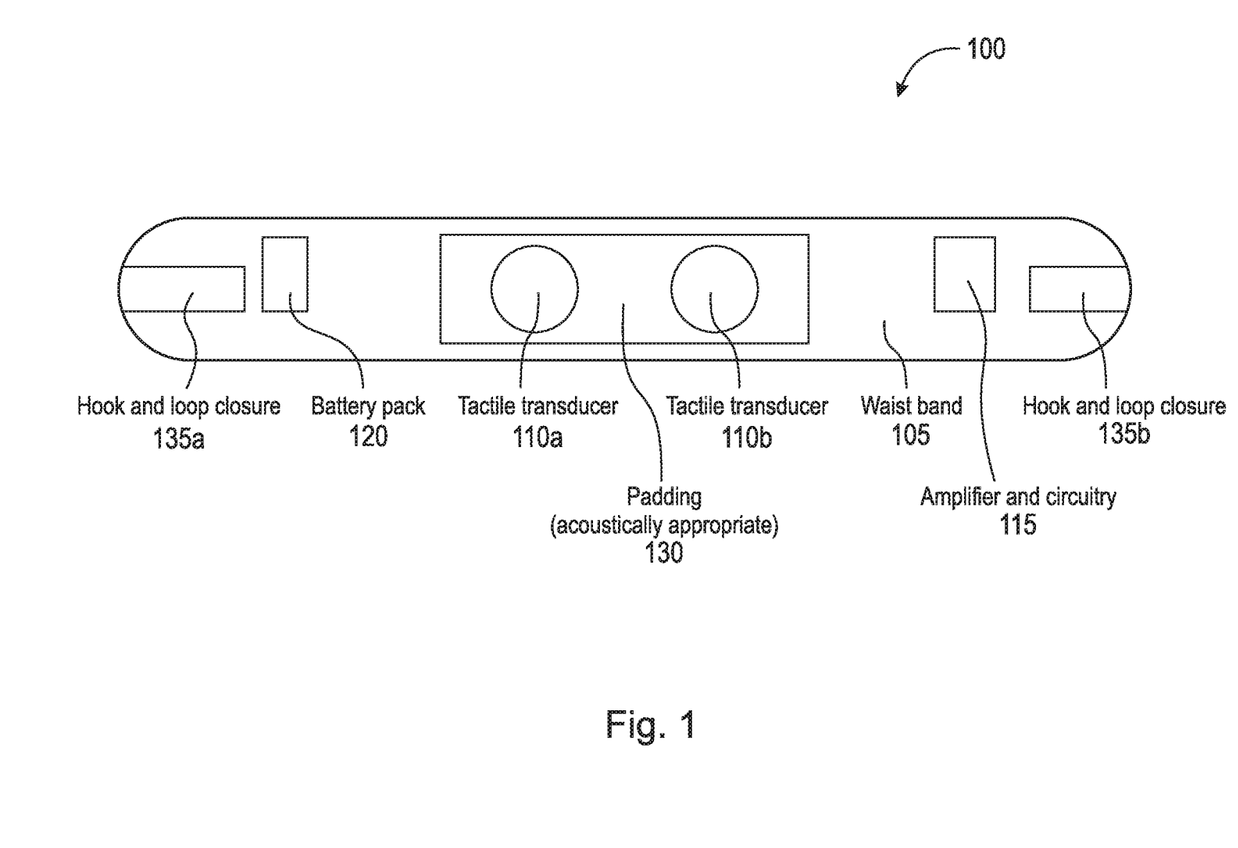
FIG. 1 is a schematic diagram illustrating an apparatus for treating kidney stones in the form of a wearable belt/band with a rechargeable battery pack, according to an example embodiment.

FIG. 1 is a schematic diagram illustrating an apparatus 100 for treating kidney stones in the form of a wearable belt/band with a rechargeable battery pack, according to an example embodiment. The example apparatus 100 includes a waist band 105 as a structural member with tactile transducers 110a,b and an amplifier and controller 115 coupled to the waist band 105. The band 105 also includes a battery pack 120 to power the tactile transducers 110a,b and amplifier and controller circuitry 115. The band 105 also includes a hook and loop closure 135a,b to secure the band 105 to an individual and padding 130 for comfort. The tactile transducers 110a,b produce mechanical waves, and the band 105 enables projection of the mechanical waves produced by the tactile transducers 110a,b toward at least one kidney of an individual wearing the band 105 to dislodge kidney stones. As used herein, "projection" of mechanical waves can include projection of the waves through any suitable medium (e.g., air, fluid, or solid object). Projection of the mechanical waves can also be referred to as and can include transfer of the mechanical waves (e.g., directly from a transducer to an individual without any intermediate medium).

Figure 2:
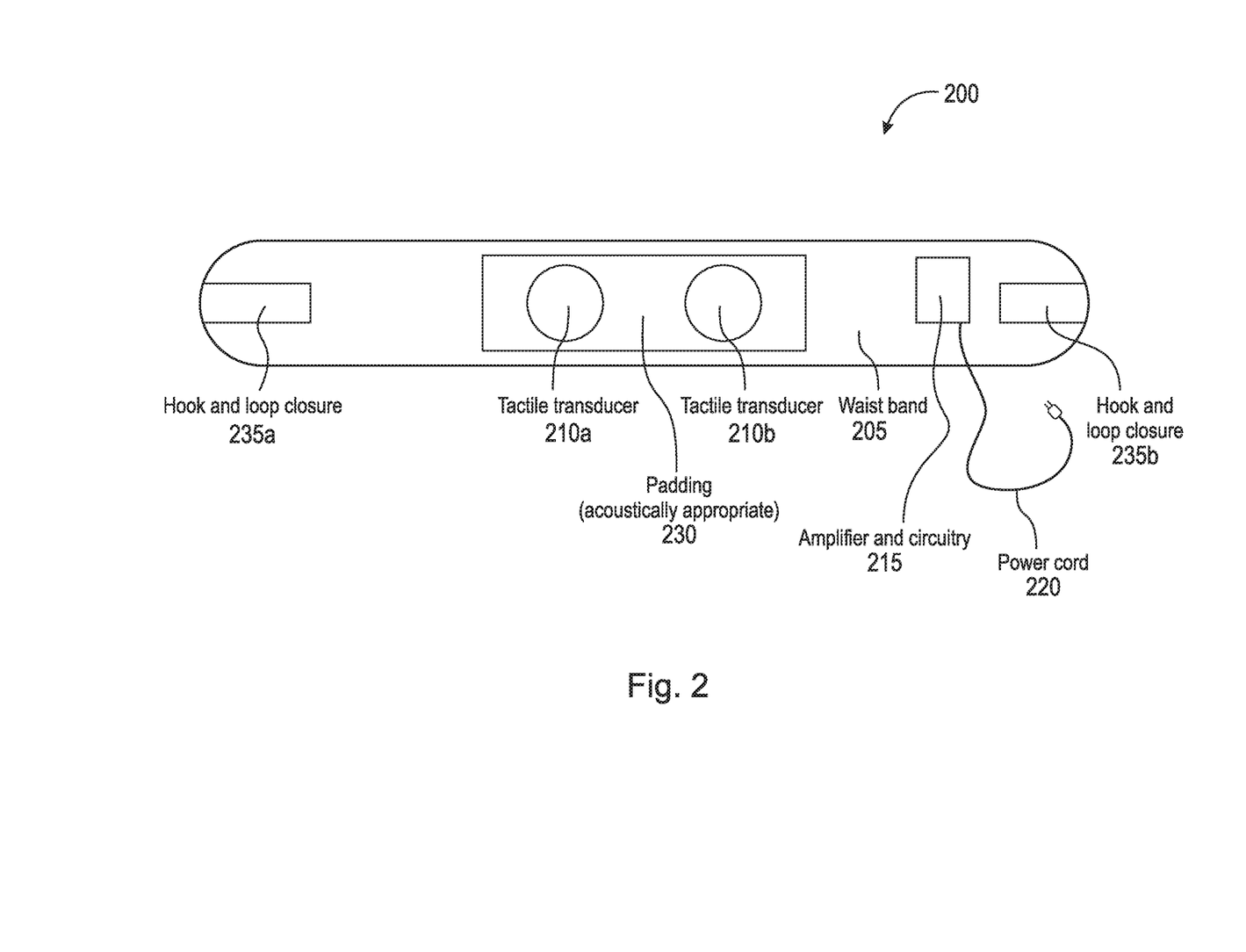
FIG. 2 is a schematic diagram illustrating an apparatus for treating kidney stones in the form of wearable belt/band with a power cord, according to an example embodiment.

FIG. 2 is a schematic diagram illustrating an apparatus 200 for treating kidney stones in the form of wearable belt/band with a power cord, according to an example embodiment. The example apparatus 200 includes a waist band 205 as a structural member with tactile transducers 210a,b and an amplifier and controller circuitry 215 coupled to the waist band 205. The band 205 also includes a power cord 220 to obtain power from a power source. The band 205 also includes a hook and loop closure 235a,b to secure the band 205 to an individual and padding 230 for comfort. The tactile transducers 210a,b produce mechanical waves, and the band 205 enables projection of the mechanical waves produced by the tactile transducers 210a,b toward at least one kidney of an individual wearing the band 205 to dislodge kidney stones.

Figure 3A:
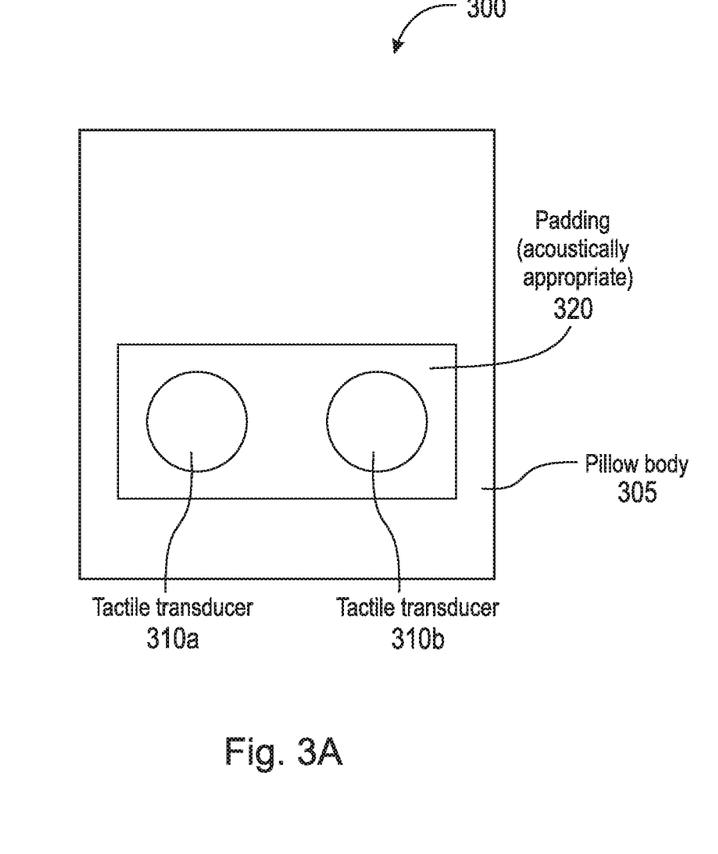
FIGS. 3A and 3B are schematic diagrams illustrating an apparatus for treating kidney stones in the form of a pillow/cushion with a rechargeable battery pack, according to an example embodiment.
Figure 3B:
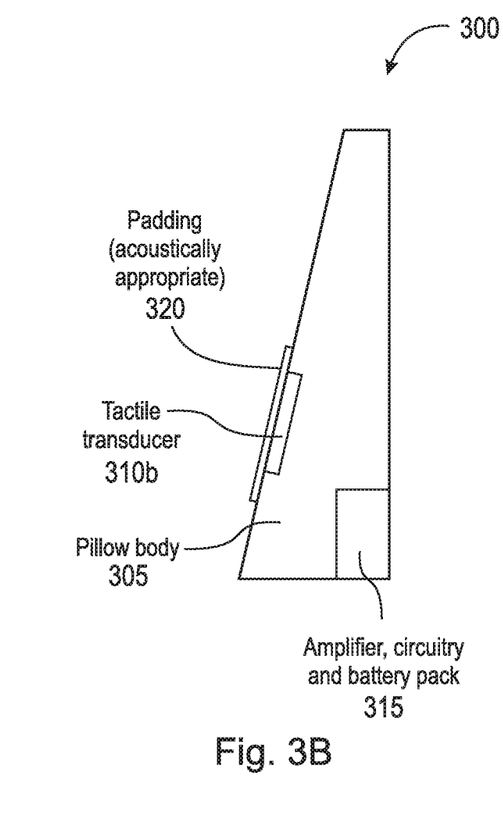

FIGS. 3A and 3B are schematic diagrams illustrating an apparatus 300 for treating kidney stones in the form of a pillow/cushion with a rechargeable battery pack, according to an example embodiment. The example apparatus 300 includes a pillow body 305 as a structural member with tactile transducers 310a,b and an amplifier, controller circuitry, and battery pack 315 coupled to the pillow body 305. The pillow body 305 also includes padding 320 for comfort. The tactile transducers 310a,b produce mechanical waves, and the pillow body 305 enables projection of the mechanical waves produced by the tactile transducers 310a,b toward at least one kidney of an individual sitting against the pillow 305 to dislodge kidney stones.

Figure 4A:
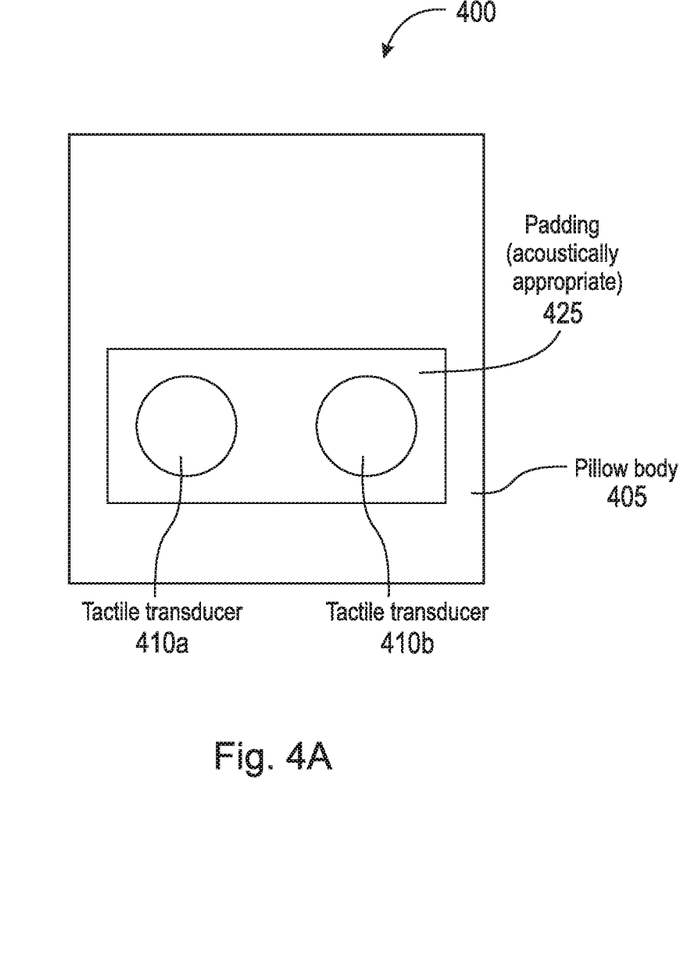
FIGS. 4A and 4B are schematic diagrams illustrating an apparatus for treating kidney stones in the form of a pillow/cushion with a power cord, according to an example embodiment.
Figure 4B:
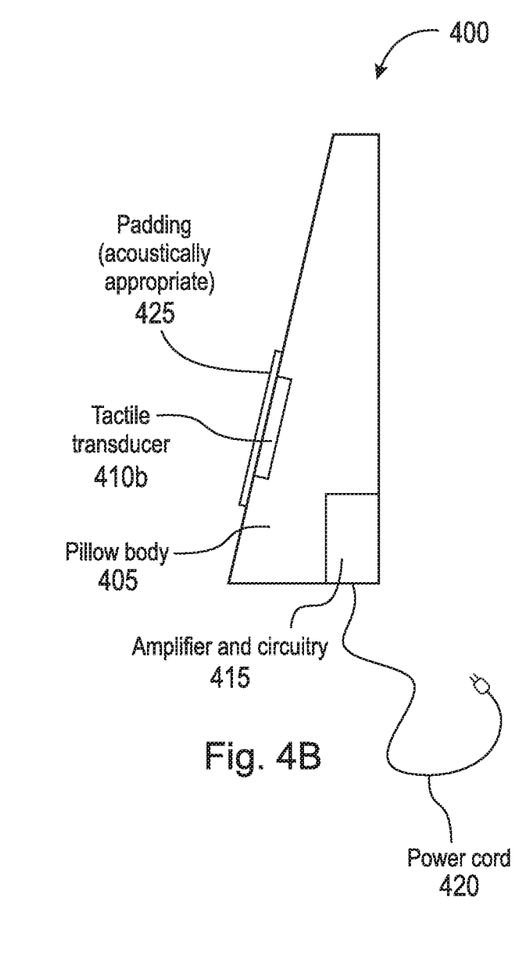

FIGS. 4A and 4B are schematic diagrams illustrating an apparatus 400 for treating kidney stones in the form of a pillow/cushion with a power cord, according to an example embodiment. The example apparatus 400 includes a pillow body 405 as a structural member with tactile transducers 410a,b and an amplifier and controller circuitry 415 coupled to the pillow body 405. The pillow body 405 also includes padding 425 for comfort and a power cord 420 to obtain power from a power source. The tactile transducers 410a,b produce mechanical waves, and the pillow body 405 enables projection of the mechanical waves produced by the tactile transducers 410a,b toward at least one kidney of an individual sitting against the pillow 405 to dislodge kidney stones.

Figure 5A:
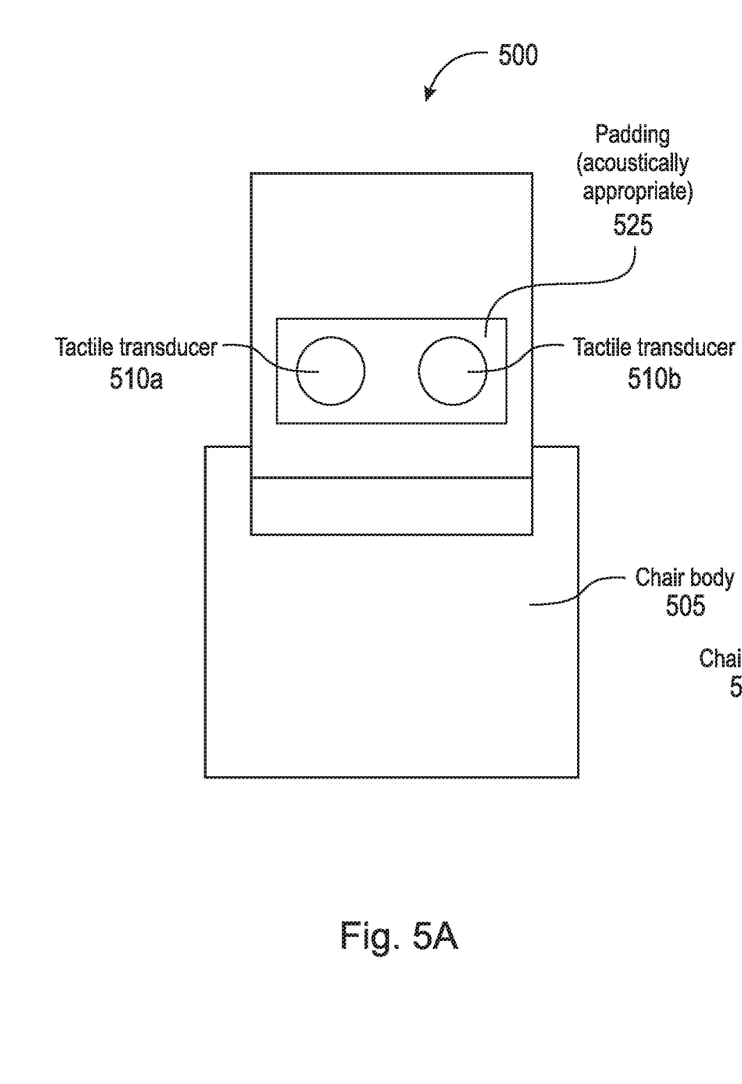
FIGS. 5A and 5B are schematic diagrams illustrating an apparatus for treating kidney stones in the form of a chair, according to an example embodiment.
Figure 5B:
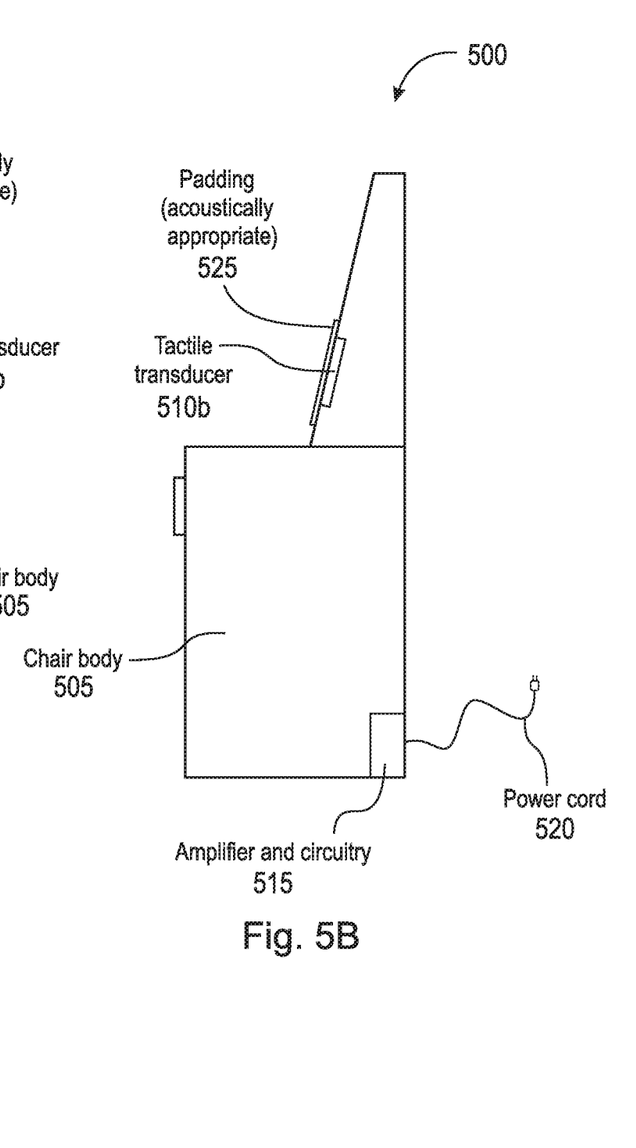

FIGS. 5A and 5B are schematic diagrams illustrating an apparatus 500 for treating kidney stones in the form of a chair, according to an example embodiment. The example apparatus 500 includes a chair 505 as a structural member with tactile transducers 510a,b and an amplifier and controller circuitry 515 coupled to the chair 505. The chair 505 also includes padding 525 for comfort and a power cord 520 to obtain power from a power source. The tactile transducers 510a,b produce mechanical waves, and the chair 505 enables projection of the mechanical waves produced by the tactile transducers 510a,b toward at least one kidney of an individual sitting on the chair 505 to dislodge kidney stones.

Figures 6A, 6B:
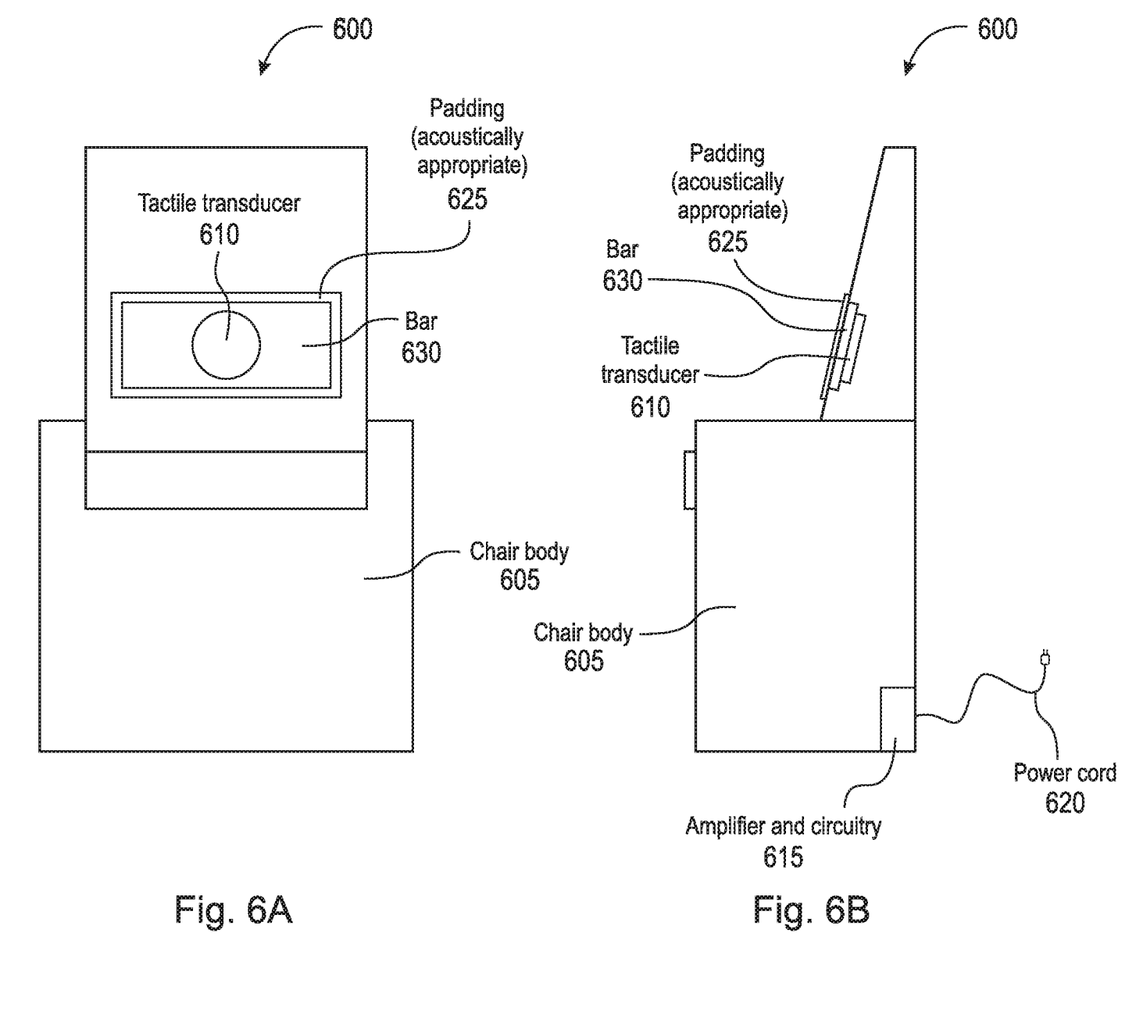
FIGS. 6A and 6B are schematic diagrams illustrating an apparatus for treating kidney stones in the form of a chair with a propagation bar, according to an example embodiment.

FIGS. 6A and 6B are schematic diagrams illustrating an apparatus 600 for treating kidney stones in the form of a chair with a propagation bar, according to an example embodiment. The example apparatus 600 includes a chair 605 as a structural member with a tactile transducer 610 and an amplifier and controller circuitry 615 coupled to the chair 605. The chair 605 also includes padding 625 for comfort, a power cord 620 to obtain power from a power source, and a bar 630 to propagate waves produced by the tactile transducer 610. The tactile transducer 610 produces mechanical waves, and the chair 605 and bar 630 enable projection of the mechanical waves, produced by the tactile transducer 610, along the bar 630 and toward at least one kidney of an individual sitting on the chair 605, to dislodge kidney stones.

Figure 7A:
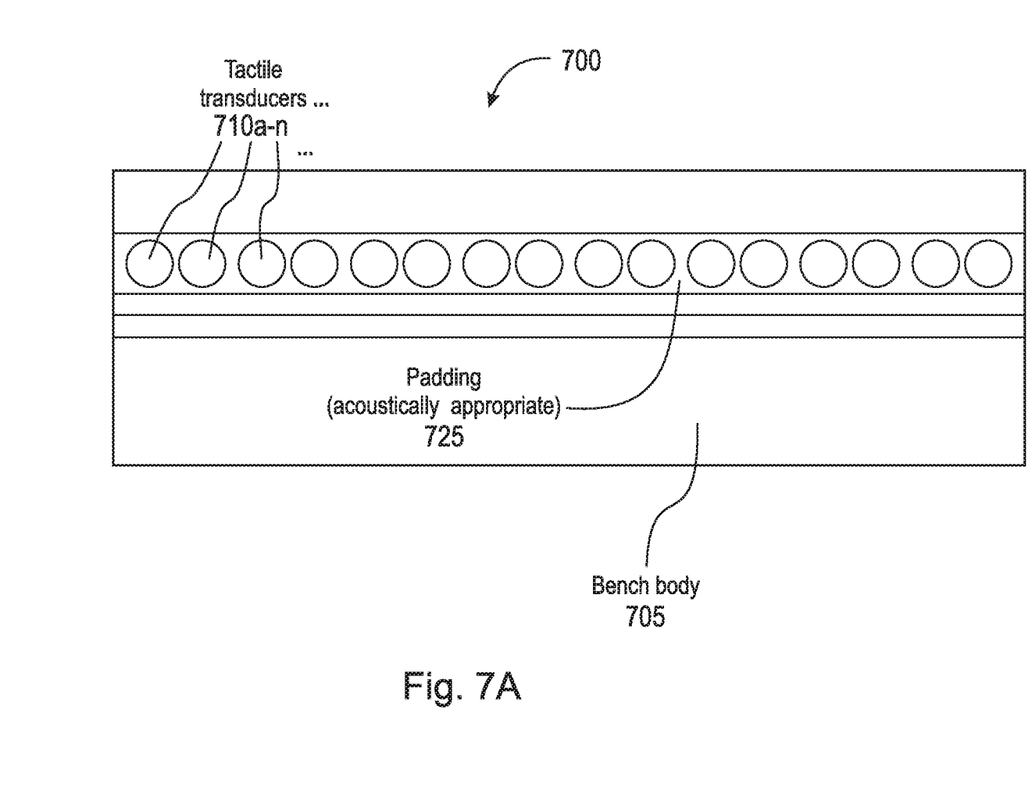
FIGS. 7A and 7B are schematic diagrams illustrating an apparatus for treating kidney stones in the form of a bench, according to an example embodiment.
Figure 7B:
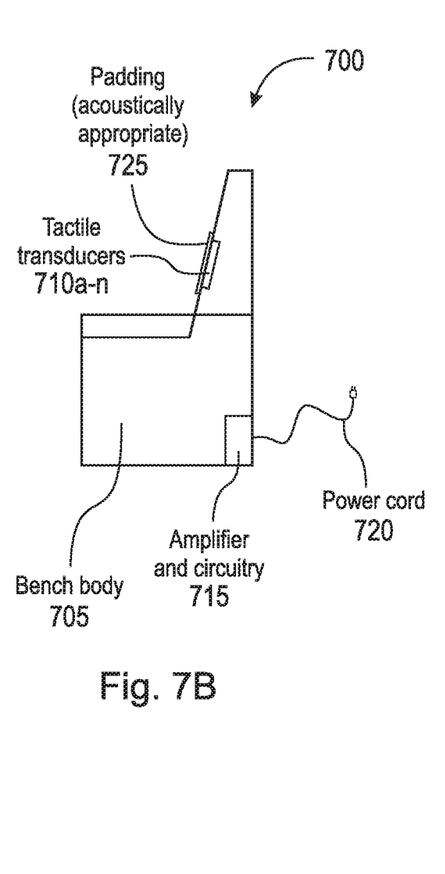

FIGS. 7A and 7B are schematic diagrams illustrating an apparatus 700 for treating kidney stones in the form of a bench, according to an example embodiment. The example apparatus 700 includes a bench 705 as a structural member with tactile transducers 710a-n and an amplifier and controller circuitry 715 coupled to the bench 705. The bench 705 also includes padding 725 for comfort and a power cord 720 to obtain power from a power source. Alternatively, the bench 705 could be powered using one or more batteries. The tactile transducers 710a-n produce mechanical waves, and the bench 705 enables projection of the mechanical waves produced by the tactile transducers 710a-n toward at least one kidney of each of a plurality of individuals sitting on the bench 705 to dislodge kidney stones.

Figure 8A:
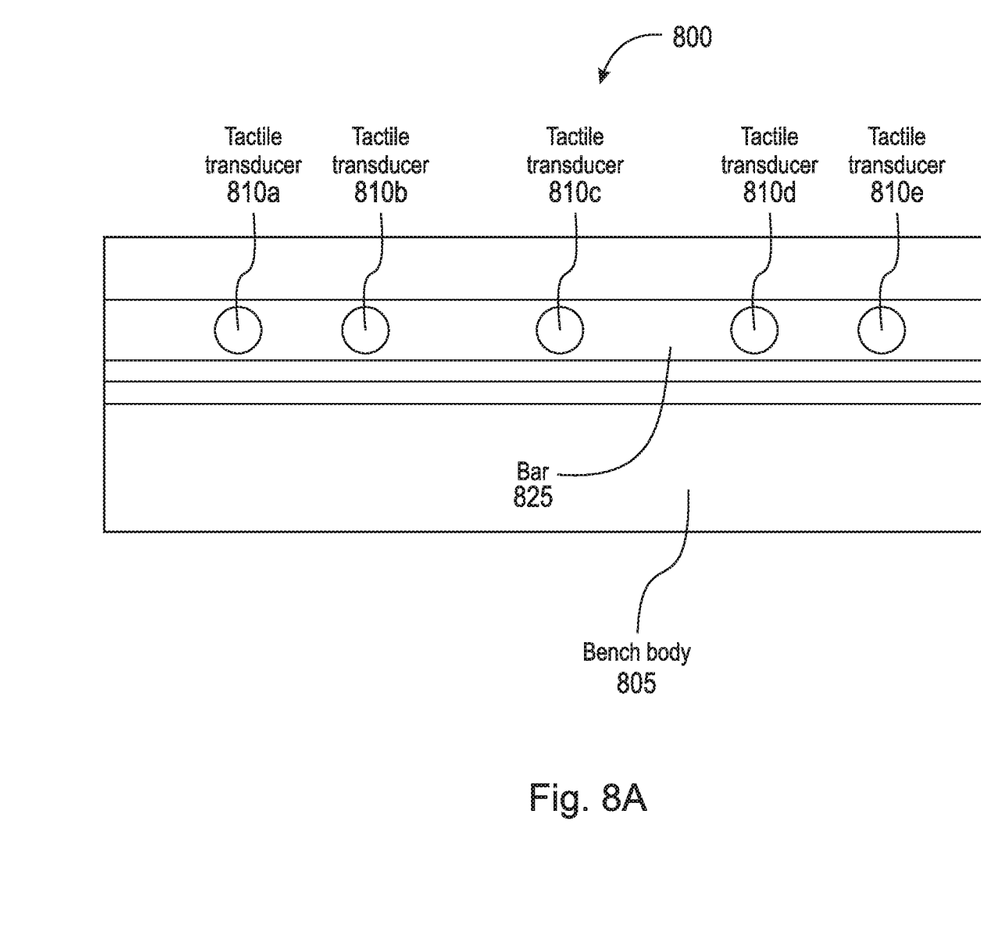
FIGS. 8A and 8B are schematic diagrams illustrating an apparatus for treating kidney stones in the form of a bench with a propagation bar, according to an example embodiment.
Figure 8B:
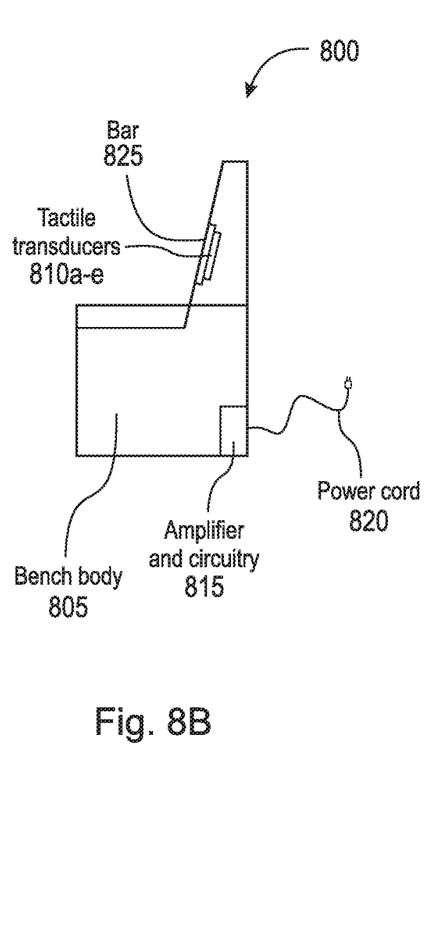

FIGS. 8A and 8B are schematic diagrams illustrating an apparatus 800 for treating kidney stones in the form of a bench with a propagation bar, according to an example embodiment. The example apparatus 800 includes a bench 805 as a structural member with tactile transducers 810a-e and an amplifier and controller circuitry 815 coupled to the bench 805. While the example apparatus 800 includes five transducers 810a-e, any number of transducers can be used. The bench 805 also includes a power cord 820 to obtain power from a power source, and a bar 825 to propagate waves produced by the tactile transducers 810a-e. Alternatively, the bench 805 could be powered using one or more batteries. The tactile transducers 810a-e produce mechanical waves, and the bench 805 and bar 825 enable projection of the mechanical waves produced by the tactile transducers 810a-e along the bar 830 and toward at least one kidney of each of a plurality of individuals sitting on the bench 805 to dislodge kidney stones.

Figure 9:
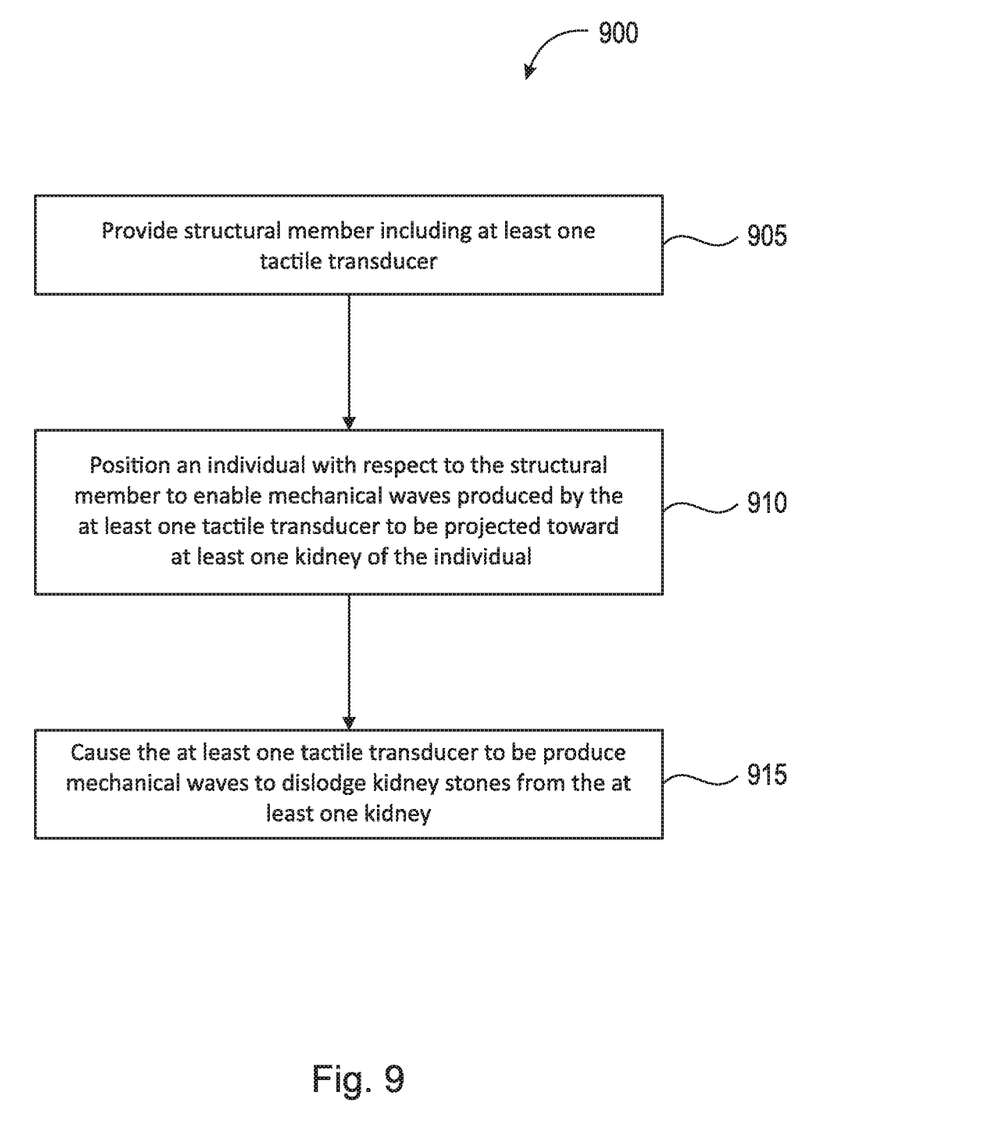
FIG. 9 is a flow diagram illustrating a method for treating kidney stones, according to an example embodiment.

FIG. 9 is a flow diagram illustrating a method 900 for treating kidney stones, according to an example embodiment. The example method 900 includes providing 905 a structural member including at least one tactile transducer configured to produce mechanical waves, positioning 910 an individual with respect to the structural member to enable the mechanical waves produced by the at least one tactile transducer to be projected toward (transferred to) at least one kidney of the individual to dislodge kidney stones from the at least one kidney, and causing 915 the at least one tactile transducer to produce mechanical waves to dislodge kidney stones from the at least one kidney. The mechanical waves may be administered for a therapeutically effective duration (e.g., in the order of minutes), and the kidney(s) of the individual may be periodically subjected to the mechanical waves.

While this invention has been particularly shown and described with references to example embodiments thereof, it will be understood by those skilled in the art that various changes in form and details may be made therein without departing from the scope of the embodiments encompassed by the appended claims.

What is claimed is:

1. An apparatus for prophylactically treating undetected kidney stones in an individual, the apparatus comprising:
    a structural member including at least one tactile transducer, the at least one tactile transducer configured to produce mechanical waves, the structural member configured to enable projection of the mechanical waves produced by the at least one tactile transducer from outside a body toward at least one kidney to prophylactically treat inconspicuous, undetected crystals that grow to form kidney stones of the at least one kidney, and wherein the structural member is any of (i) a band configured to be worn by the individual and to be arranged to position the at least one tactile transducer to project the mechanical waves toward at least one of the individual's kidneys, (ii) a cushion configured to allow the individual to position a part of the individual's body against the cushion with the at least one tactile transducer positioned to project the mechanical waves toward at least one of the individual's kidneys, (iii) a chair and the at least one tactile transducer is mounted to the chair so that the at least one tactile transducer is configured to be positioned to project the mechanical waves toward the individual's kidneys when the individual is sitting in the chair, (iv) a bench and the at least one tactile transducer includes a plurality of tactile transducers mounted to the bench, each of the plurality of tactile transducers configured to be positioned to project the mechanical waves toward at least one kidney of an individual sitting on the bench, and (v) a bar bench and the at least one tactile transducer is mounted to a bar spanning at least a portion of the length of the bar bench and configured such that, when a plurality of individuals are sitting on the bar bench, the mechanical waves produced by the at least one tactile transducer propagate along the bar and toward the at least one kidney of each of the plurality of individuals;
    an amplifier electronically coupled to the at least one tactile transducer; and
    a controller electronically coupled to the amplifier and configured to determine the mechanical waves produced by the at least one tactile transducer, the controller configured to cause the at least one tactile transducer to produce mechanical waves at a wave frequency in the range of nine to sixteen hertz.

2. An apparatus as in claim 1 wherein the structural member includes two tactile transducers configured to be mounted at locations corresponding to positions of two kidneys.

3. An apparatus as in claim 1 wherein the at least one tactile transducer is adjustably mounted to the structural member.

4. An apparatus as in claim 1 further comprising padding mounted to the at least one tactile transducer.

5. An apparatus as in claim 1 further including at least one vibration isolator mounted between the structural member and the at least one tactile transducer.

6. An apparatus as in claim 1 wherein the controller is configured to cause the at least one tactile transducer to cycle through the frequency range of mechanical waves.

7. An apparatus as in claim 1 wherein the controller is configured to cause the at least one tactile transducer to continuously ramp through the frequency range of mechanical waves.

8. An apparatus for administering mechanical waves to an individual for the purpose of prophylactically treating undetected kidney stones, the apparatus comprising:
    a structural member including at least one tactile transducer, the at least one tactile transducer configured to produce mechanical waves, the structural member configured to enable projection of the mechanical waves produced by the at least one tactile transducer from outside the individual toward the individual to prophylactically treat inconspicuous, undetected crystals that grow to form kidney stones, and wherein the structural member is any of (i) a band configured to be worn by the individual, (ii) a cushion configured to allow the individual to position a part of the individual's body against the cushion, (iii) a chair, and (iv) a bench including a plurality of tactile transducers mounted to the bench;
    an amplifier electronically coupled to the at least one tactile transducer; and
    a controller electronically coupled to the amplifier and configured to determine the mechanical waves produced by the at least one tactile transducer, the controller configured to cause the at least one tactile transducer to produce mechanical waves at a resonant wave frequency of kidney tissue.

9. An apparatus as in claim 8 wherein the structural member is a bar bench and the at least one tactile transducer is mounted to a bar spanning at least a portion of the length of the bar bench so that, when a plurality of individuals are sitting on the bar bench, the mechanical waves produced by the at least one tactile transducer propagate along the bar and toward the plurality of individuals.

10. A method of prophylactically treating undetected kidney stones in an individual, the method comprising:
    providing a structural member including at least one tactile transducer configured to produce mechanical waves, wherein the structural member is any of (i) a band configured to be worn by the individual, (ii) a cushion configured to allow the individual to position a part of the individual's body against the cushion, (iii) a chair, and (iv) a bench including a plurality of tactile transducers mounted to the bench;
    positioning the individual with respect to the structural member to enable the mechanical waves produced by the at least one tactile transducer to be projected from outside the individual toward at least one kidney of the individual to prophylactically treat inconspicuous, undetected crystals that grow to form kidney stones of the at least one kidney; and causing the at least one tactile transducer to produce mechanical waves in the wave frequency range of nine to sixteen hertz to prophylactically treat kidney stones of the at least one kidney.

11. A method as in claim 10 wherein causing the at least one tactile transducer to produce mechanical waves includes causing the at least one tactile transducer to cycle through a range of frequencies.

12. A method as in claim 10 further comprising positioning multiple individuals with respect to the structural member to enable the mechanical waves produced by the at least one tactile transducer to be projected toward at least one kidney of each of the multiple individuals.

13. A method as in claim 10 wherein the mechanical waves are administered for a therapeutically effective duration.

14. A method as in claim 10 further comprising periodically subjecting the at least one kidney of the individual to mechanical waves produced by the at least one tactile transducer.

15. A method as in claim 10 further comprising causing the at least one tactile transducer to continuously ramp through the range of frequencies.

16. A method as in claim 10, wherein the at least one kidney has not been imaged.

17. A method of claim 10, wherein the at least one kidney has not been scanned.

18. A method of claim 10, wherein the at least one kidney has not been imaged for a period of time during which a kidney stone would remain inconspicuous.

19. A method of claim 10, wherein the at least one kidney has not been subjected to imaging radiation.

\* \* \* \* \*